United States Patent [19]

Suehiro et al.

[11] 3,989,682

[45] Nov. 2, 1976

[54] PROCESS FOR PREPARING 2-THIOADENOSINE

[75] Inventors: Hideo Suehiro; Kiyomi Kikugawa, both of Kokubunji; Motonobu Ichino; Tokuro Nakamura, both of Mitaka, all of Japan

[73] Assignee: Kohjin Co., Ltd., Tokyo, Japan

[22] Filed: July 14, 1975

[21] Appl. No.: 595,834

[30] Foreign Application Priority Data

July 12, 1974 Japan................................ 49-79239
Oct. 28, 1974 Japan.............................. 49-123441
Jan. 7, 1975 Japan................................. 50-4259
May 26, 1975 Japan.............................. 50-61921

[52] U.S. Cl. ................................................. 536/23
[51] Int. Cl.$^2$........................................ C07H 19/22
[58] Field of Search ............................. 260/211.5 R

[56] References Cited
UNITED STATES PATENTS 3,872,082   3/1975   Bergmeyer et al........... 260/211.5 R

OTHER PUBLICATIONS

Cresswell, et al. "J. Org. Chem.", 28 p. 2560, 1963.

Yamazaki, et al. J. Org. Chem. 32, p. 3032, 1967.

Primary Examiner—Johnnie R. Brown
Attorney, Agent, or Firm—Sughrue, Rothwell, Mion, Zinn & Macpeak

[57] ABSTRACT

A process for preparing 2-thioadenosine, useful as an intermediate for the preparation of S-substituted-2-thioadenosines having a platelet aggregation inhibitory activity and a coronary vasodilating activity, which comprises reacting 5-amino-1-β-D-ribofuranosylimidazole-4-carboxamide oxime or an O-substituted oxime thereof with carbon disulfide in a closed reaction zone at a temperature of from about 50° to about 200° C in a solvent.

4 Claims, No Drawings

PROCESS FOR PREPARING 2-THIOADENOSINE

BACKGROUND OF THE INVENTION

1. FIELD OF THE INVENTION

This invention relates to a process for preparing 2-thioadenosine which is an intermediate for the preparation of S-substituted-2-thioadenosines, useful as a platelet aggregation inhibitor and a coronary vasodilator.

2. DESCRIPTION OF THE PRIOR ART

It is well known that S-substituted-2-thioadenosines possess excellent pharmacological activities. Above all, a certain type of S-substituted-2-thioadenosines is known to have a coronary vasodilating activity as reported in M. H. Maguire et al., *J. Med. Chem.*, 14, 415 (1971); J. A. Angus et al., *Brit. J. Pharmacol.*, 41, 592 (1971); R. Einstein et al., *Europ. J. Pharmacol.*, 19, 246 (1972); and L. B. Cobbin et al., *Brit. J. Pharmacol.*, 50, 25 (1974) and a platelet aggregation inhibitory activity as reported in G. V. R. Born et al., *Nature*, 205, 678 (1965); F. Michal et al., Nature, 222, 1073 (1969); M. A. Packham et al., *Amer. J. Physiol.*, 223, 419 (1972); and K. Kikugawa et al., *J. Med. Chem.*, 16, 1381 and 1389 (1973). It is also known that 2-thioadenosine is an advantageous intermediate for producing these useful S-substituted-2-thioadenosines as disclosed in K. Kikugawa et al., *J. Med. Chem.*, 16, 1381 (1973).

The conventionally known processes for preparing the above 2-thioadenosine include two methods. One method comprises reacting 2-chloroadenosine which is obtained from naturally occurring guanosine via four steps in a 10% yield with sodium hydrogen sulfide to obtain 2-thioadenosine in a 70% yield (overall yield, 7%) as disclosed by K. Kikugawa et al. in *J. Med. Chem.*, 16 1381 (1973). The other method comprises 3 steps wherein 5-amino-4-cyano-1-β-D-ribofuranosylimidazole (AICN-riboside) is formed from naturally occurring 5-amino-1-β-D-ribofuranosylimidazole-4-carboxamide (AICA-riboside) plus an additional 3 steps herein 2-benzylthioadenosine is obtained in a 20% yield, and then followed by reduction with liquid ammonia-sodium to obtain 2-thioadenosine in a 50% yield (overall yield, 10%) as disclosed by R. Marumoto et al. in *Chem. Pharm. Bull. (Japan)*, 23, 759 (1975). However, both of these conventional methods involve extremely complicated reaction steps as a prerequisite for the production of the desired compound, and are not industrially practical when the resulting 2-thioadenosine is contemplated as a starting material for the production of S-substituted-2-thioadenosines.

Recent investigations have been made on processes for preparing 2-thioadenosine starting with a material that can easily be obtained from natural products in high yield.

The following several processes are known for cyclizing a 5-amino-4-substituted-imidazole ring using carbon disulfide to form a purine ring and incorporating a mercapto group into the 2-position of the purine ring.

5-Amino-1-β-D-ribofuranosylimidazole-4-carboxamide is heated to 180° C with carbon disulfide in methanolic sodium hydroxide to obtain sodium 2-thioinosine (as disclosed in A. Yamazaki et al., *J. Org. Chem.*, 32, 3032 (1967)).

5-Amino-1-cyclopentylimidazole-4-carboxamidine is reacted with carbon disulfide in dimethylformamide containing a suspension of anhydrous potassium carbonate at room temperature to obtain 9-cyclopentyl-2-thioadenine (as disclosed in J. A. Montgomery and H. J. Thomas, J. Med. Chem., 15, 182 (1972)).

5-Amino-4-cyano-1-β-D-ribofuranosylimidazole is reacted with carbon disulfide in pyridine to obtain 2,6-dithio-9-β-D-ribofuranosylpurine (as disclosed in R. Marumoto et al., *Chem. Pharm. Bull. (Japan)*, 23, 759 (1975)).

4-Aminoimidazole-5-carboxamide oxime is reacted with carbon disulfide in pyridine and methanol at room temperature to obtain 2-thioadenine 1-N-oxide (as disclosed in R. M. Cresswell and G. B. Brown, *J. Org. Chem.*, 28, 2560 (1962)).

All these conventional processes comprise cyclization of a 4-carboxamide, 4-cyano, 4-carboxamidine or 4-carboxamide oxime type 5-aminoimidazole, in which a purine ring having a mercapto group introduced into the 2-position thereof can be formed simply by effecting a ring-closure using carbon disulfide.

Instead of the carbon disulfide employed above, 5-amino-1-β-D-ribofuranosylimidazole-4-carboxamidine is reacted with 1,1'-thiocarbonyldiimidazole in dimethyl sulfoxide to obtain 5-amino-1-β-D-ribofuranosylimidazole-4-carboxamidine cyclic 3',5'-phosphate (as disclosed in Japanese Patent Application Laid Open to Public Inspection No. 109395/1974 published on Oct. 17, 1974 (corresponding to U.S. Patent Application Serial No. 330,306 filed Feb. 7, 1973) and R. B. Meyer et al., *J. Amer. Chem. Soc.*, 96, 4962 (1974)). However, this process is disadvantageous in that the reagent, 1,1'-thiocarbonyldiimidazole, is too expensive to use in industrial production, and the product can only be obtained in a yield of as low as 48%.

Further, when a 4-carboxamide or 4-cyano type 5-amino-imidazole is cyclized with carbon disulfide for the purpose of preparing 2-thioadenosine, a number of subsequent working-up steps from 2-thioinosine to 2-thioadenosine are required until the final product can be obtained as reported, e.g., in R. Marumoto et al., *Chem. Pharm. Bull. (Japan)*, 23, 759 (1975). The purpose may be accomplished by reacting a 4-carboxamidine type 5-aminoimidazole with carbon disulfide. However, as shown in the above cited references [*J. Med. Chem.*, 15, 182 (1974) and J. Amer. Chem. Soc., 96, 4962 (1974)], the starting material can first be obtained through 4 required reaction steps starting from adenosine and, consequently, the total yield of this process is low.

4-Carboxamide oximes or the O-substituted derivatives thereof which are used as a starting material for the production of the 4-carboxamidine type 5-aminoimidazoles can be obtained starting with adenosine via 2 to 3 reaction steps with a high yield. However, when the cyclization of the resulting 5-aminoimidazoles is effected with carbon disulfide, these starting oximes remain in the reaction product as an N-oxide or an O-substituted-N-oxide of 2-thioadenosine. Removal of the resulting N-oxides or O-substituted-N-oxide group can generally be carried out by reduction, but the procedures involved therein are not always easy. For example, only one instance of reduction in a purine ring N-oxide is reported in T. Fujii and T. Itaya, *Tetrahedron*, 27, 351 (1971). Furthermore, the fact that the purine ring has a mercapto group in the 2-position would make it difficult to carry out a selective oxidation of the N-oxide, which, in fact, has never been attempted in the art.

SUMMARY OF THE INVENTION

Accordingly, this invention provides a process for preparing 2-thioadenosine, an intermediate for the production of 8-substituted-2-thioadenosines, of the formula

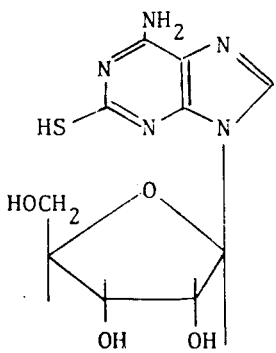

which comprises reacting a 5-amino-1-β-D-ribofuranosylimidazole-4-carboxamide oxime or an O-substituted oxime thereof represented by the formula (I)

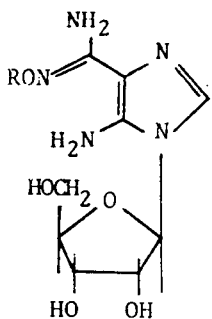

(I)

wherein R represents a hydrogen atom; a straight or branched chain alkyl group having 1 to 10 carbon atoms; a cycloalkyl group having 5 to 8 carbon atoms; a benzyl group which may be mono-substituted with a halogen atom or an alkyl or alkoxy group having 1 to 4 carbon atoms at the o-, m-, or p-position of the aryl moiety thereof; or a 1- or 2-naphthyl group; with carbon disulfide in a closed reaction zone at a temperature of from about 50° to about 200° C in the presence of a solvent.

DETAILED DESCRIPTION OF THE INVENTION

The term "straight or branched chain alkyl group having 1 to 10 carbon atoms" as used herein for R designates groups such as methyl, ethyl, propyl, isopropyl, n-butyl, iso-butyl, sec-butyl, tert-butyl, pentyl, hexyl, heptyl, octyl, nonyl, decyl and like groups.

The term "cycloalkyl group having 5 to 8 carbon atoms" as used herein for R designates groups such as cyclopentyl, cyclohexyl, cycloheptyl, cyclooctyl and like groups.

The term "halogen atom" as used herein as a substituent on the benzyl group includes fluorine, chlorine, bromine and iodine atoms.

The alkyl group having 1 to 4 carbon atoms as a substituent on the benzyl group includes methyl, ethyl, propyl, iso-propyl, butyl, iso-butyl, sec-butyl, and tert-butyl groups.

The alkoxy group having 1 to 4 carbon atoms as a substituent on the benzyl group includes methoxy, ethoxy, propoxy, iso-propoxy, butoxy, iso-butoxy, sec-butoxy and tert-butoxy groups.

The 5-amino-1-β-D-ribofuranosylimidazole-4-carboxamide oxime or an O-substituted oxime thereof having the formula (I) which can be used as a starting material in the present invention can be either in the free state or in the form of an acid addition salt such as a hydrochloride, a formate, an acetate and the like thereof.

The hydroxyl groups in the ribofuranosyl moiety of the formula (I) can be protected with an acyl group, such as an acetyl, benzoyl or a like group, in which case the acylated compound of the formula (I) can be deacylated during the reaction under suitable reaction conditions, preferably under alkaline conditions. Further, the hydroxyl groups on the 3'- and 5'-positions can also be in the phosphorylated form, but in which case the phosphorylated compound of the formula (I) cannot be dephosphorylated during the reaction, and the compound (I) can be obtained by dephosphorylation after completion of the reaction.

The starting compound of the formula (I) wherein R is a hydrogen atom can easily be prepared from adenosine-N-oxide (as disclosed in M. A. Stevens et al., J. Amer. Chem. Soc., 81, 1734 (1959)). The compound of the formula (I) wherein R is a benzyl group can be prepared from 1-benzyloxyadenosine (as disclosed in J. A. Montgomery and H. J. Thomas, Chem. Comm., 458 (1969)) and the compounds of the formula (I) wherein R is an alkyl, cycloalkyl, substituted-benzyl or naphthyl group can easily be obtained from a 1-alkoxy or a 1-aralkoxy adenosine (as disclosed in T. Fujii et al., Chem. Pharm. Bull. (Japan), 19, 1368 (1971) and W. M. Shannon et al., J. Med. Chem., 17, 361 (1974)). All of these compounds from which the compound of the formula (I) can be prepared can be obtained via 2 to 3 reaction steps starting from adenosine in a high yield.

The compound of the formula (I) prepared as described above can be used in the process according to the present invention, either with or without isolation from the reaction mixture obtained. For example, 5-amino-1-β-D-ribofuranosylimidazole-4-carboxamide oxime represented by the fomula (I) wherein R is a hydrogen atom can easily be prepared by decomposing adenosine-1-N-oxide in an alkali metal hydroxide solution and passing the reaction mixture over an ion-exchange resin such as Diaion SK-1B (ammonium-type, a tradename, manufactured by Mitsubishi Chemical Industries, Ltd., Japan), Diaion SK-1B (H⁺-type, a tradename, manufactured by Mitsubishi Chemical Industries, Ltd., Japan), Diaion WK-11 (H⁺-type, a tradename, manufactured by Mitsubishi Chemical Industries, Ltd., Japan), Amberlite IRC-50 (H⁺-type, a tradename, manufactured by Rohm & Haas) and the like to adsorb sodium followed by concentration. The thus obtained starting material, i.e., the compound of the formula (I), need not be isolated. Further, although the starting material obtained contains moisture, there is no need to remove the water from the starting material since the subsequent reaction can be conducted in an aqueous reaction system as shown in Embodiments I and II hereinafter described in detail.

The process according to the present invention for the preparation of 2-thioadenosine comprises reacting a starting material dissolved in a solvent with carbon disulfide in a closed reaction zone, e.g., in an autoclave, at a temperature from about 50° to 200° C. The process includes the following three embodiments, each of which is characterized by the solvent used. That is, Embodiment I comprises reacting the 5-amino-1-β-D-ribofranosyl-imidazole-4-carboxamide oxime or the O-substituted oxime represented by the formula (I) with carbon disulfide in water or an aqueous medium having a pH of about 3 to 12. Embodiment II comprises reacting the compound of the formula (I) with an alkali metal xanthogenate prepared in situ by reacting (1) an alcohol, (2) an alkali metal or an alkali metal hydroxide and (3) carbon disulfide in an alcohol which may be the same as or different from the above alcohol. Embodiment III comprises reacting the compound of the formula (I) with carbon disulfide in an organic solvent in the presence of a tertiary amine. From the standpoint of yield and cost, Embodiment I above is preferred.

The characteristics of the process according to the present invention include the following:

1. the starting material, 5-amino-1-β-D-ribofuranosyl-imidazole-4-carboxamide or an O-substituted oxime thereof, of the formula (I) can be easily obtained starting from naturally occurring adenosine in a high yield;

2. the reaction with carbon disulfide is carried out by heating in a closed reaction zone at a temperature of from about 50° to about 200° C under autogenous pressure (e.g., 5 to 20 Kg/cm²), and low cost reagents are employed;

3. the cyclization effected by the heating in the closed reaction zone at the above recited temperature range leads to a selective and quantitative reduction in the —N—OR group at the 1-position of the resulting closed ring as well as the introduction of a mercapto group into the 2-position. This reduction can be considered to be caused by the hydrogen sulfide generated during the course of the reaction between the starting material of the formula (I) and carbon disulfide. The reduction results in a selective and quantitative reaction to remove the RO-group without adversely affecting the mercapto group introduced into the 2-position; and 4. the reaction involving the cyclization and the reduction in the —N—OR group in one step provides a yield of more than about 65%, with an almost quantitative yield of the product being obtained under optimum reaction conditions. Thus, the overall yield obtained according to the process of this invention through 3 to 4 reaction steps starting from naturally occurring adenosines can reach higher than about 50%, and it becomes even higher, e.g., above about 80%, when the reaction is conducted under optimum conditions.

In carrying out Embodiment I of the present invention, the starting material of the formula (I) is dissolved in about 0.5 to about 50 ml of water per mole of the compound of the formula (I), and carbon disulfide is added to the aqueous solution in an amount of about an equimolor amount to about 500 moles, preferably 5 to 50 moles, per mole of the starting material. The resulting mixture is heated in a closed reaction zone such as an autoclave at a temperature of from about 50° to about 200° C, preferably 80° to 150° C, under autogenous pressure for a period of from about 1 to about 10 hours. The pH of the aqueous solution having the starting material dissolved therein is maintained at about 3 to about 12, preferably 7 to 10 from the standpoint of yield of the desired product. When the pH is below about 3, the aqueous solution should be adjusted to a pH within the above pH range using an alkali metal hydroxide such as sodium hydroxide and potassium hydroxide, ammonia or an amine such as pyridine, trimethylamine, triethylamine, α-picoline, etc. When the pH is above about 12, the adjustment to the above recited pH range can be effected with, for example, an acid such as hydrochloric acid, acetic acid, sulfuric acid, formic acid and the like, or an ion-exchange resin such as Diaion SK-1B (H⁻-type), Diaion WK-11 (H⁻-type), Amberlite IRC-50 (H⁻-type and the like. The above described aqueous medium can contain an inert organic solvent in an amount up to about 95% concentration. Suitable inert organic solvents which can be used include an alcohol, such as methanol, ethanol, isopropanol, amyl alcohol, benzyl alcohol, etc., dimethylformamide, formamide, dimethylacetamide, acetonitrile, dimethyl sulfoxide and the like.

The mixture comprising the aqueous solution of the starting material and carbon disulfide tends to be a two-phase system under ordinary pressure, but this does not adversely affect the reaction at all. After completion of the reaction, the reaction mixture is concentrated to dryness, and the concentrate is dissolved in aqueous ammonia. Any impurities are removed by filtration, and the filtrate is adjusted to a pH of about 1 to 4 to crystalize the product thereby obtaining 2-thioadenosine.

In Embodiment II of the present invention, suitable alcohols which can be used as one of the reactants and/or a reaction solvent include methanol, ethanol, iso-propanol, amyl alcohol, benzyl alcohol and the like. Examples of alkalis which can be used in this reaction are alkali metals, such as sodium and potassium, and alkali metal hydroxides, such as sodium hydroxide and potassium hydroxide. In carrying out the reaction, about an equimolar amount to about 500 moles, preferably 5 to 50 moles, of carbon disulfide and about an equimolar amount to about 500 moles, preferably 5 to 50 moles, of the alkali are employed per mole of the starting material of the formula (I), respectively. This reaction can be conducted in a homogeneous system in about 10 to 1000 moles of the above described alcohol per mole of the starting material at a temperature ranging from about 50° to about 200° C, preferably 80° to 150° C, for a period of from about 1 to 10 hours.

In Embodiment III of this invention, preferred tertiary amines which can be used include pyridine, triethylamine and the like. Since these amines act as a solvent as well as a basic catalyst, there is no need to affirmatively employ a solvent. However, an organic solvent which does not interfere with the reaction such as an alcohol, e.g., methanol, ethanol, iso-propanol, amyl alcohol, benzyl alcohol, etc., dimethylformamide, formamide, dimethylacetamide, acetonitrile, dimethyl sulfoxide and the like can be used.

The above reaction can be carried out using about an equimolar amount to about 500 moles, preferably 5 to 50 moles, of each of the tertiary amine and the carbon disulfide per mole of the starting material of the formula (I) in a homogeneous reaction system at a temperature of from about 50° to about 200° C, preferably 100° to 150° C, for a period of from about 1 to 12 hours.

As described above, the 2-thioadenosine produced by the process of this invention is useful as a starting material to produce various S-substituted-2-thioadenosines, which are useful as platelet aggregation inhibiting agents and coronary vasodilating agents, e.g., as disclosed in copending U.S. patent application Ser. Nos. 371,340 filed June 19, 1973; 378,116 filed July 10, 1973; 378,117 filed July 10, 1973; and 568,491 filed Apr. 16, 1975; the disclosure of which is incorporated herein by reference.

The present invention is further illustrated by reference to the following examples, but they are given for illustrative purposes only and the invention is not to be construed as being limited to these examples. In these examples, all parts, percents, ratios and the like are by weight unless otherwise indicated.

EXAMPLE 1

16g of adenosine 1-oxide monohydrate (53.3 mmol) was refluxed in 150 ml of a 5N sodium hydroxide aqueous solution for 15 minutes. The resulting liquid was neutralized to a pH of 9.0 using Amberlite IRC-50 ($H^+$-type). Water was then added thereto to make the total volume 400 ml. To this was added 100 ml of carbon disulfide, and the mixture was reacted in an autoclave at a temperature of 120° C for a period of 5 hours under autogenous pressure (about 10 $Kg/cm^2$). The orange colored substance thus formed was recovered followed by concentration to dryness. The residue was dissolved in 125 ml of 2.5N aqueous ammonia, and any impurities contained were filtered out. A mixture of n-butanol and acetic acid (250 ml:125 ml) was added to the filtrate to crystallize the product to obtain 16.5 g of 2-thioadenosine having a melting point of 198° C (with decomposition) in a 98% yield. UV Absorption Spectrum: $_{max}{}^{pH\ 1}$ 238.5 nm ($\epsilon$:13800) and 293 nm ($\epsilon$:18400); $_{max}{}^{pH13}$ 243 nm ($\epsilon$:19100) and 283 nm ($\epsilon$:14000).

Elemental Analysis: Calcd. for $C_{10}H_{13}O_4N_5S \cdot H_2O$(%): C, 37.89; H, 4.77; N, 22.09; S, 10.12. Found (%): C, 37.53; H, 4.79; N, 22.13; S, 10.22.

EXAMPLE 2

8.0 g of adenosine 1-oxide monohydrate (26.67 mmol) was refluxed in 5 ml of a 5N sodium hydroxide aqueous solution for 15 minutes. The resulting liquid was neutralized to a pH of 9.0 using Amberlite IRC-50 ($H^+$-type) and then concentrated to a small volume to prepare 5-amino-1-$\beta$-D-ribofuranosylimidazole-4-carboxamide oxime. To this was added 200 ml of an aqueous solution containing 175 ml of methanol. The pH of the resulting solution was 9. 50 ml of carbon disulfide was further added to the solution, and the mixture was allowed to react in an autoclave at 120° C for 5 hours under autogenous pressure (about 10 $Kg/cm^2$). The orange colored substance formed in the autoclave was removed and concentrated to dryness. The residue was dissolved in 63 ml of 2.5N aqueous ammonia, and any impurities were filtered out. A mixture of n-butanol and acetic acid (125 ml:63 ml) was added to the above filtrate to crystallize the product to obtain 8.20 g of 2-thioadenosine having a melting point of 199° C (with decomposition) in a 97% yield.

EXAMPLE 3

10.0 g of 5-amino-1-$\beta$-D-ribofuranosylimidazole-4-carboxamide oxime hydrochloride was dissolved in 200 ml of an aqueous solution containing 175 ml of methanol, and the resulting solution was adjusted to a pH of 9 with sodium hydroxide. 50 ml of carbon disulfide was added to the solution, and the mixture was allowed to react in an autoclave at a temperature of 120° C for 5 hours under autogenous pressure (about 10 $Kg/cm^2$) followed by working up in the same manner as described in Example 1 to obtain 9.7 g of 2-thioadenosine having a melting point of 198° C (with decomposition) in a 95% yield.

EXAMPLE 4

0.45 g of 5-amino-1-$\beta$-D-ribofuranosylimidazole-4-carboxamide O-ethyl-oxime was dissolved in 8 ml of an aqueous solution containing 7 ml of methanol, and 2 ml of carbon disulfide was added to the solution. The resulting mixture was allowed to react in an autoclave at 120° C for 6 hours under autogenous pressure (about 10 $Kg/cm^2$). The reaction mixture was concentrated to dryness, and the residue was dissolved in water. The aqueous solution was adjusted to a pH of 2 with hydrochloric acid, and the crystals thus precipitated were filtered to obtain 2-thioadenosine, which was then dissolved in aqueous ammonia, filtered and again adjusted to a pH of 2 with hydrochloric acid to obtain 0.355 g of pure 2-thioadenosine having a melting point of 199° C (with decomposition) in a 75% yield.

EXAMPLE 5

0.45 g of 5-amino-1-$\beta$-D-ribofuranosylimidazole-4-carboxamide O-cyclohexyl-oxime was dissolved in 4 ml of an aqueous solution containing 3 ml of N,N-dimethylformamide, and 1 ml of carbon disulfide was added to the solution. The resulting mixture was allowed to react in an autoclave at 125° C for 5 hours under autogenous pressure (about 10 $Kg/cm^2$), and the reaction product was worked up in the same manner as described in Example 1 to obtain 0.305 g of 2-thioadenosine having a melting point of 197° C (with decomposition) in 76% yield.

EXAMPLE 6

0.45 g of 5-amino-1-$\beta$-D-ribofuranosylimidazole-4-carboxamide O-(p-methylbenzyl)-oxime was dissolved in 8 ml of an aqueous solution containing 1 ml of ethanol, and 2 ml of carbon disulfide was added to the solution. The resulting mixture was allowed to react in an autoclave at 130° C for 5 hours under autogenous pressure (about 10 $Kg/cm^2$), and the reaction product was worked up in the same manner as described in Example 1 to obtain 0.288 g of 2-thioadenosine having a melting point of 198° C (with decomposition) in a 76% yield.

EXAMPLE 7

8.0 g of adenosine 1-oxide (26.67 mmol) was refluxed in 75 ml of a 5N sodium hydroxide aqueous solution for 15 minutes. The resulting liquid was neutralized to a pH of 5.0 with Amberlite IRC-50 ($H^+$-type) and concentrated to a small volume to prepare 1-$\beta$-D-ribofuranosyl-5-aminoimidazole-4-carboxamide oxime. To this was added 200 ml of an aqueous solution containing 175 ml of methanol, the resulting solution being found to have a pH of 9. 50 ml of carbon disulfide was added to the solution, and the mixture was allowed to react in an autoclave at 120° C for 5 hours under autogenous pressure (about 10 $Kg/cm^2$). The orange colored substance formed was removed and concentrated to dryness. The residue was dissolved in 63 ml of 2.5N aqueous ammonia, and any impurities were filtered out. A mixture of n-butanol and acetic acid (125 ml:63 ml) was added to the filtrate to crystallize the product to obtain 5.42 g of 2-thioadenosine having a melting point of 199° C (with decomposition) in a 92% yield.

EXAMPLE 8

0.45 g of 5-amino-1-$\beta$-D-ribofuranosylimidazole-4-carboxamide O-(p-methylbenzyl)-oxime was dissolved in a mixture of 0.30g of sodium hydroxide, 5 ml of methanol and 0.5 ml of carbon disulfide, and the resulting mixture was allowed to react in an autoclave at 130° C for 4 hours under autogenous pressure (about 10 Kg/cm$^2$). The reaction mixture was concentrated to dryness, and the residue was dissolved in water. The resulting aqueous solution was adjusted to a pH of 2 with hydrochloric acid, and the precipitated crystals were filtered to obtain crude 2-thioadenosine. The crude product was dissolved in aqueous ammonia, filtered and adjusted to a pH of 2 with hydrochloric acid to obtain 0.27 g of pure 2-thioadenosine having a melting point of 198° C (with decomposition) in a 72% yield.

EXAMPLE 9

0.45 g of 5-amino-1-(2,3,5-tri-O-acetyl-$\beta$-D-ribofuranosyl)imidazole-4-carboxamide O-benzyl-oxime was dissolved in a mixture of 0.30 g of sodium hydroxide, 5 ml of methanol and 0.5 ml of carbon disulfide, and the resulting mixture was allowed to react in an autoclave at 170° C for 4 hours under autogenous pressure (about 12 - 13 Kg/cm$^2$). The reaction product was worked up in the same manner as described in Example 7 to obtain 0.265 g of 2-thioadenosine having a melting point of 198° C (with decomposition) in a 91% yield.

EXAMPLE 10

To 10.0 g of 5-amino-1-$\beta$-D-ribofuranosylimidazole-4-carboxamide oxime hydrochloride were added 120 ml of methanol and 120 ml of pyridine to form a solution. 60 ml of carbon disulfide was added to the solution, and the resulting mixture was allowed to react in an autoclave at 120° C for 3 hours under autogenous pressure (about 10 kg/cm$^2$). The reaction mixture was concentrated to dryness, and the residue was dissolved in 1N aqueous ammonia. 100 ml of n-butanol and 50 ml of glacial acetic acid were then added to the solution followed by cooling to crystallize the product to obtain 9.01 g of 2-thioadenosine having a melting point of 199° C (with decomposition) in an 88% yield.

EXAMPLE 11

9.6 g of adenosine 1-oxide monohydrate was refluxed together with 45 ml of a 5N sodium hydroxide aqueous solution for a period of 15 minutes. Water was added thereto to make the total volume 200 ml, and the resulting aqueous solution was passed through a column packed with 300 ml of Diaion SK-1B (ammonium-type), and the column was washed with water. The effluent and the washings were combined (about 2 liters) and concentrated to dryness. 120 ml of methanol and 120 ml of pyridine were added to the residue to form a solution, and 60 ml of carbon disulfide was added thereto. The resulting mixture was allowed to react in an autoclave at 120° C for 6 hours under autogenous pressure (about 10 kg/cm$^2$). The reaction mixture was concentrated to dryness, and the residue was suspended in about 50 ml of water. The precipitate formed in the suspension was filtered and then washed with 50 ml of 1N aqueous ammonia. To the washing were added 100 ml of n-butanol and 50 ml of glacial acetic acid followed by cooling to obtain 9.06 g of 2-thioadenosine having a melting point of 199° C (with decomposition) as crystals in a 95% yield.

EXAMPLE 12

In the same manner as described in Example 11, 9.6 g of adenosine 1-oxide monohydrate was treated with a 5N sodium hydroxide aqueous solution and Diaion SK-1B (ammonium-type). 60 ml of N,N-dimethylformamide and 60 ml of triethylamine were added to the resulting residue to form a solution, and 30 ml of carbon disulfide was then added to the solution. The resulting mixture was allowed to react in an autoclave at 130° C for 4 hours under autogenous pressure (about 10 kg/cm$^2$). The reaction mixture was concentrated to dryness followed by working up in the same manner as described in Example 11 to obtain 9.35 g of 2-thioadenosine as crystals having a melting point of 198° C (with decomposition) in a 98% yield.

EXAMPLE 13

In the same manner as described in Example 11, 9.6 g of adenosine 1-oxide monohydrate was treated with a 5N sodium hydroxide aqueous solution and Diaion SK-1B (ammonium-type) to obtain a residue. 200 ml of pyridine and then 60 ml of carbon disulfide were added to the above residue, and the resulting mixture was allowed to react in an autoclave at 120° C for 5 hours under autogenous pressure (about 10 Kg/cm$^2$). The reaction mixture was concentrated to dryness, and the residue was worked up in the same manner as described in Example 11 to obtain 9.35 g of 2-thioadenosine as crystals having a melting point of 197° C (with decomposition) in a 98% yield.

EXAMPLE 14

0.45 g of 5-amino-1-$\beta$-D-ribofuranosylimidazole-4-carboxamide O-benzyl-oxime was dissolved in a mixture of 0.3 ml of pyridine, 5 ml of methanol and 0.5 ml of carbon disulfide, and the resulting mixture was allowed to react in an autoclave at 150° C for 10 hours under autogenous pressure (about 10–12 Kg/cm$^2$). The reaction mixture was concentrated to dryness, and the residue was dissolved in water. Hydrochloric acid was added thereto to adjust the pH of the aqueous solution to 2. The thus precipitated crystals were filtered to obtain crude 2-thioadenosine, which was then dissolved in aqueous ammonia followed by filtration. The filtrate was adjusted to a pH of 2 with hydrochloric acid to obtain 0.295 g of a crystalline pure product having a melting point of 199° C (with decomposition) in a 75% yield.

EXAMPLE 15

0.45 g of 5-amino-1-$\beta$-D-ribofuranosylimidazole-4-carboxamide O-ethyl-oxime was dissolved in a mixture of 0.3 ml of pyridine, 5 ml of methanol and 0.5 ml of carbon disulfide. The resulting mixture was allowed to react in an autoclave at 120° C for 6 hours under autogenous pressure (about 10 Kg/cm$^2$). The reaction mixture was concentrated to dryness, and the residue was dissolved in water. The aqueous solution was adjusted to a pH of 2 with hydrochloric acid to precipitate the crude product, which was then recovered by filtration. The filter cake was dissolved in aqueous ammonia, the solution was filtered, and the filtrate was adjusted to a pH of 2 with hydrochloric acid to obtain 0.31 g of pure 2-thioadenosine as crystals having a melting point of 199° C (with decomposition) in a 65% yield.

EXAMPLE 16

0.45 g of 5-amino-1-β-D-ribofuranosylimidazole-4-carboxamide O-cyclohexyl-oxime was dissolved in a mixture of 0.2 ml of triethylamine and 5 ml of N,N-dimethylformamide, and 0.5 ml of carbon disulfide was further added to the solution. The resulting mixture was allowed to react in an autoclave at 125° C for 5 hours under autogenous pressure (about 10 Kg/cm²) followed by working up in the same manner as described in Example 15 to obtain 0.26 g (yield, 65%) of 2-thioadenosine having a melting point of 197° C (with decomposition).

While the invention has been described in detail and with reference to specific embodiments thereof, it will be apparent to one skilled in the art that various changes and modifications can be made therein without departing from the spirit and the scope thereof.

What is claimed is:

1. A process for preparing 2-thioadenosine comprising reacting a 5-amino-1-β-D-ribofuranosylimidazole-4-carboxamide oxime or an O-substituted oxime thereof represented by the formula (I)

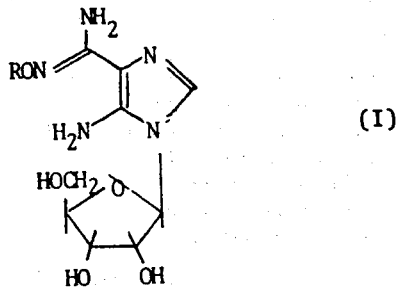

(I)

wherein R represents a hydrogen atom, a straight or branched chain alkyl group having 1 to 10 carbon atoms, a cycloalkyl group having 5 to 8 carbon atoms, a benzyl group which may be mono-substituted with a halogen atom or an alkyl or alkoxy group having 1 to 4 carbon atoms at the o, m or p-position thereof, or a 1 or 2-naphthyl group, with carbon disulfide in water or an aqueous medium as a solvent at pH of about 3 to about 12. in a closed reaction zone at a temperature of from about 50° to about 200° C.

2. The process as claimed in claim 1, wherein the amount of said carbon disulfide ranges from about an equimolar amount to about 500 moles per mole of said 5-amino-1-β-D-ribofuranosylimidazole-4-carboxamide oxime or an O-substituted oxime thereof.

3. The process as claimed in claim 1, wherein said solvent is at pH of 7 to 10.

4. The process as claimed in claim 1, wherein said aqueous liquid medium contains an inert organic solvent selected from the group consisting of methanol, ethanol, isopropanol, amyl alcohol, benzyl alcohol, dimethyl formamide, formamide, dimethyl acetamide, acetonitrile and dimethyl sulfoxide.

* * * * *